United States Patent [19]

Gardner

[11] 4,234,726
[45] Nov. 18, 1980

[54] HETEROCYCLIC CONTAINING CHROMANS

[75] Inventor: Derek V. Gardner, Bishop Stortford, England

[73] Assignee: Beecham Group Limited, England

[21] Appl. No.: 37,958

[22] Filed: May 9, 1979

Related U.S. Application Data

[60] Continuation of Ser. No. 852,744, Nov. 18, 1977, abandoned, which is a division of Ser. No. 691,865, Jun. 1, 1976, Pat. No. 4,093,631.

[30] Foreign Application Priority Data

Jun. 3, 1975 [GB] United Kingdom ............... 24005/75

[51] Int. Cl.³ .................. C07D 413/12; C07D 405/12
[52] U.S. Cl. .................................... 544/151; 544/376; 546/196; 260/326.34; 260/326.5 S; 260/326.5 SF; 260/326.5 D
[58] Field of Search ............... 544/151, 376; 546/196; 260/326.5 S, 326.5 CF, 326.5 D, 326.34, 345.2

[56] References Cited

U.S. PATENT DOCUMENTS

| 4,079,066 | 3/1978 | Gardner | 424/248.55 |
|---|---|---|---|
| 4,146,539 | 3/1979 | Gardner | 546/196 |

Primary Examiner—Henry R. Jiles
Assistant Examiner—R. W. Ramsuer
Attorney, Agent, or Firm—Jacobs & Jacobs

[57] ABSTRACT

Compounds of the formula (I):

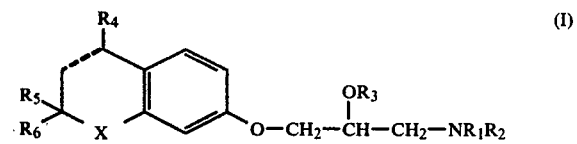

or a pharmaceutically acceptable salt thereof wherein the $NR_1R_2$ moiety is a 5-, 6-, or 7-membered saturated heterocyclic ring; $R_3$ is hydrogen, alkyl of 1 to 4 carbon atoms or acyl of 1 to 4 carbon atoms; $R_4$ is naphthyl or phenyl unsubstituted or substituted by one or two substituents selected from the group consisting of fluorine, chlorine, bromine, methoxyl, benzyloxyl, trifluoromethyl, methyl, cyano, nitro, acetoxyl, amino, methylamino, ethylamino, dimethylamino, diethylamino, acetamide, hydroxyl, methoxycarbonyl, ethoxycarbonyl, carboxamido, sulphonamido, carboxy, trifluoromethylthio, trifluoromethoxyl, methylsulphonyl, trifluomethylsulphonyl and methylthio; $R_5$ is hydrogen or alkyl of 1 to 4 carbon atoms; $R_6$ is hydrogen or alkyl of 1 to 4 carbon atoms; X is oxygen and the dotted line represents a single or double bond.

23 Claims, No Drawings

HETEROCYCLIC CONTAINING CHROMANS

CROSS-REFERENCE

This is a continuation of Ser. No. 852,744 filed Nov. 18, 1977, now abandoned, which is a divisional of Ser. No. 691,865 filed June 1, 1976, now U.S. Pat. No. 4,093,631.

The present invention relates to novel compounds, to their preparation and to pharmaceutical compositions containing them.

Belgian Pat. No. 831,939 discloses inter alia pharmaceutically active compounds of the formula (O):

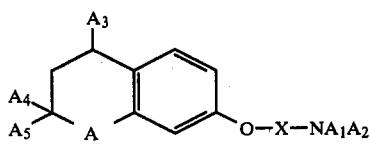

wherein X is an alkylene group of 2-4 atoms, A is an oxygen atom or —$CH_2$— group; $A_1$ is a hydrogen atom or $C_{1-6}$ alkyl group, $A_2$ is a hydrogen atom, a $C_{1-6}$ alkyl, phenyl, tolyl or benzyl group or $A_2$ is linked to $A_1$ so that $NA_1A_2$ is a 5-, 6-, or 7- membered saturated ring; $A_3$ is an aryl group and $A_4$ and $A_5$ are each hydrogen atoms or $C_{1-4}$ alkyl groups.

Other compounds have now been found which possess pharmacological activity and the present invention is concerned with these compounds and with intermediates for their preparation.

Accordingly, the present invention provides compounds of the formula (I):

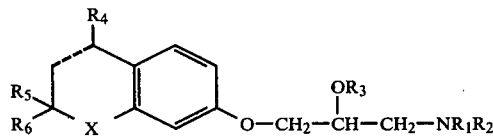

and salts thereof wherein $R_1$ is a hydrogen atom or a $C_{1-4}$ alkyl or benzyl group; $R_2$ is a hydrogen atom or a $C_{1-4}$ alkyl group or is joined to $R_1$ so that the $NR_1R_2$ moiety is a 5-, 6- or 7-membered saturated heterocyclic group; $R_3$ is hydrogen or a $C_{1-4}$ alkyl or $C_{1-4}$ acyl group; $R_4$ is an aromatic group; $R_5$ is a hydrogen atom or a $C_{1-4}$ alkyl group; $R_6$ is a hydrogen atom or a $C_{1-4}$ alkyl group; X is —$CH_2$ or an oxygen atom and the dotted line represents a single or double bond.

In general the compounds of the formula (I) wherein the dotted line is a single bond are envisaged as pharmaceutical agents while the corresponding compounds wherein the dotted line is a double bond are intermediates for their preparation.

Suitably $R_1$ is a hydrogen atom or a methyl or ethyl group. Preferably $R_1$ is a hydrogen atom or methyl group.

Suitably $R_2$ is a $C_{1-4}$ alkyl group or is joined to $R_1$ to form a 5- or 6-membered saturated heterocyclic group. Most suitably $R_2$ is a methyl or ethyl group or is joined to $R_1$ to form a piperidino, morpholino, pyrrolidino or piperazino group. Preferably $R_2$ is a methyl group.

Suitably $R_3$ is a hydrogen atom.

The term "aromatic group" when used herein means a naphthyl or optionally substituted phenyl group. The term "optionally substituted phenyl group" when used herein means a phenyl group or a phenyl group substituted by one or two substitutents chosen from amongst fluorine, chlorine or bromine atoms or methoxyl, benzyloxyl, trifluoromethyl, methyl, cyano, nitro, acetoxyl, amino, methylamino, ethylamino, dimethylamino, diethylamino, acetamido, hydroxyl, methoxycarbonyl, ethoxycarbonyl, carboxamido, sulphonamido, carboxy, trifluoromethylthio, trifluoromethoxyl, methylsulphonyl, trifluoromethylsulphonyl or methylthio groups.

Suitably $R_4$ is a phenyl group, a naphthyl group or a phenyl group optionally substituted by a hydrogen, fluorine, chlorine or bromine atom or a methyl, methoxy, hydroxy, trifluoromethyl or nitro group.

Suitably $R_5$ and $R_6$ are both methyl groups.

Most suitably X is an oxygen atom.

Particularly suitable compounds within formula (I) include those of formula (II):

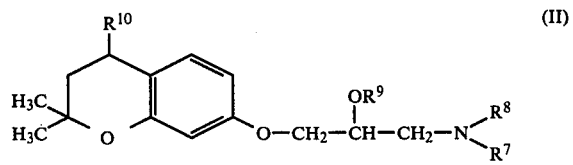

and salts thereof wherein $R_7$ is a hydrogen atom or a methyl or ethyl group; $R^8$ is a $C_{1-4}$ alkyl group or is linked to $R^7$ to form a 5- or 6-membered saturated heterocyclic group; $R^9$ is a hydrogen atom or an acetyl group and $R^{10}$ is a phenyl or naphthyl group or a mono-substituted phenyl group.

Suitably $R^7$ is a hydrogen atom or a methyl group.

Suitably $R^8$ is a methyl or ethyl group or is joined to $R^7$ to form a piperidino, morpholino, pyrrolidino or piperazino group.

Suitably $R^9$ is a hydrogen atom.

Suitably $R^{10}$ is a phenyl or 2-naphthyl group or a phenyl group substituted by a fluorine, chlorine or bromine atom or by a methyl, methoxy, hydroxy, trifluoromethyl or nitro group.

One particularly suitable group of compounds useful in the treatment of depression is that of formula (III):

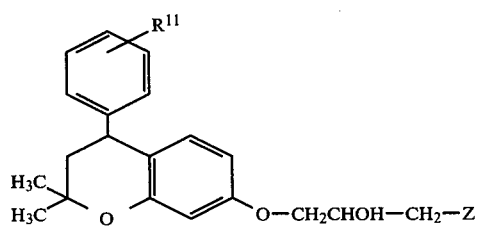

or a salt thereof wherein $R^{11}$ is a hydrogen, fluorine, chlorine or bromine atom or a methyl, methoxy, or trifluoromethyl group, and Z is a methylamino, dimethylamino, morpholino, piperidino, pyrrolidino or N-methylpiperazino group.

More suitably $R^{11}$ is a hydrogen, fluorine or chlorine atom or methyl, methoxy or trifluoromethyl group.

One preferred substituent $R^{11}$ is the trifluoromethyl group, especially the 3-trifluoromethyl group.

A further preferred substituent $R^{11}$ is the hydrogen atom.

Preferably Z is a methylamino or dimethylamino group.

Further particularly suitable groups of compounds useful in the treatment of depression include those of the formulae (IV) and (V):

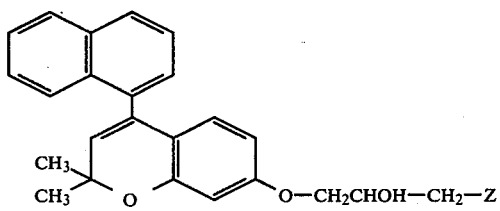
(IV)

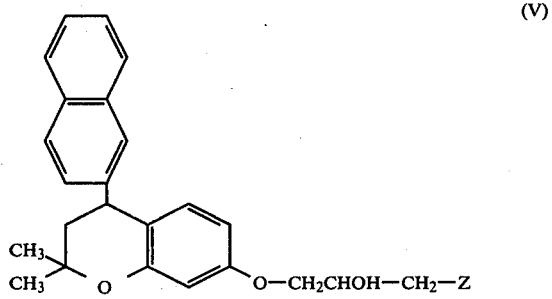
(V)

wherein Z is a group as defined in relation to formula (III).

Suitably Z is a methylamino or dimethylamino group.

A particularly suitable group of compounds useful for the induction of anorexia is that of the formula (VI):

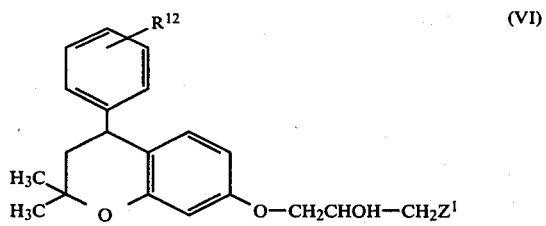
(VI)

wherein $R^{12}$ is a hydrogen atom or a trifluoromethyl group and $Z^1$ is a methylamino or dimethylamino group.

Most suitably $Z^1$ is a dimethylamino group.

Preferably $R^{12}$ is a 4-trifluoromethyl group.

The compounds of the present invention have a chiral centre at the 4-position of the chroman nucleus. The preferred compounds of this invention have the same configuration at the 4-position as (−)-2,2-dimethyl-7-(2-dimethylaminoethoxy)-4-(3-trifluoromethylphenyl)-chroman hydrochloride.

Since the compounds of this invention are nitrogenous bases they are able to form acid addition salts in conventional manner. Normally, such salts are those formed from pharmaceutically acceptable organic or inorganic acids such as citric, acetic, propionic, benzoic, lactic, tartaric, mandelic, succinic, fumaric, oleic, glutamic, gluconic, methanesulphonic, toluenesulphonic, sulphuric, phosphoric, hydrobromic, hydrochloric, or the like acid. As will be recognized by those familiar with the formulation of pharmaceutical agents, the nature of the salting acid is relatively unimportant as long as it forms a stable and preferably crystalline pharmaceutically acceptable acid addition salt. Certain compounds within this invention and their salts are able to form solvates such as hydrates, for example, monohydrates.

Compounds within the formula (I) affect the central nervous system. Thus depending on the dosage used, certain compounds of the formula (I) are able to produce anorexic or mood modifying effects in mammals.

Accordingly, in one of its aspects the present invention provides pharmaceutical compositions which comprise a compound of this invention as hereinbefore described together with a pharmaceutically acceptable carrier.

Normally, the compositions of this invention are adapted for oral administration to humans although compositions adapted for parenteral administration are also envisaged.

The most suitable dosage forms are unit dosage forms such as tablets, capsules, sachets and the like which contain a predetermined quantity of active material.

Such unit dosage forms normally contain from 0.5 to 250 mg. and preferably from 2.5 mg. to 125 mg. of active material and may be taken once a day or several times a day according to the dose desired. Generally a human adult will be administered from 0.5 to 1000 mgs per day.

If the composition of this invention is intended for the introduction of anorexia the composition will normally be in the form of a solid unit dosage form which contains from 2 mg. to 150 mg. of active ingredient.

If the composition of this invention is intended for mood-modification such as anti-depressant effects, it is likely that it will be used as a solid unit dosage form which contains from 0.5 to 50 mg. of active ingredient, for example 1 mg. to 25 mg. of active ingredient.

In a further aspect this invention provides a method of suppressing appetite, which comprises administering an anorexically effective amount of a compound of this invention.

In a further aspect this invention provides a method of reducing depression, which comprises administering an anti-depressively effective amount of a compound of this invention.

The useful anorexic activity of compounds of this invention may be determined by the oral administration to hungry rats of the compound and measuring the reduction in their food intake. The results given in Table 1 were obtained for compounds of the formula (VII):

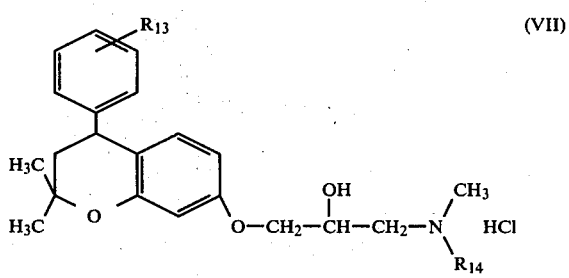
(VII)

TABLE 1

Anorexic Activity of Some Compounds of the Invention

| $R_{13}$ | $R_{14}$ | Approximate Dose REquired to Reduce Food Intake by 50% (mg/kg) |
|---|---|---|
| 3-$CF_3$ | $CH_3$ | 3.0 |
| 4-$CF_3$ | $CH_3$ | 18 |

TABLE 1-continued

Anorexic Activity of Some Compounds of the Invention

| $R_{13}$ | $R_{14}$ | Approximate Dose REquired to Reduce Food Intake by 50% (mg/kg) |
|---|---|---|
| H | $CH_3$ | 3.6 |

The useful mood-modifying activity of the compounds of this invention may be determined by standard tests such as the Reserpine Prevention test which demonstrates the ability of the compounds to prevent reserpine-induced hypothermia in mice. The results given in Table 2 were obtained for compounds of the formula (VIII):

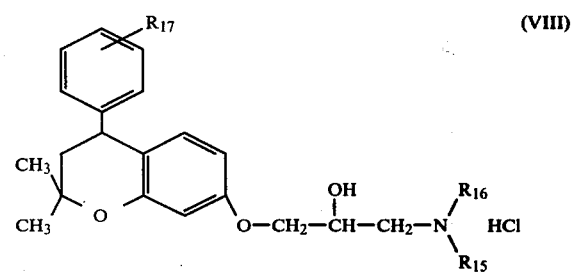

(VIII)

TABLE 2

Dose at which Certain Compounds of the Invention are Active on the Reserpine Prevention Test in Mice

| $R_{15}$ | $R_{16}$ | $R_{17}$ | Approximate Dose Required mg/kg | Min. Dose (mg/kg) at which deaths occured |
|---|---|---|---|---|
| $CH_3$ | $CH_3$ | 4-$CF_3$ | 10 | 100 |
| H | CH(CH$_3$)$_2$ | H | 3 | 100 |
| $CH_3$ | $CH_3$ | H | 0.3 | 30 |
| $CH_3$ | H | H | 0.3 | * |
| $CH_3$ | $CH_3$ | 3-$CF_3$ | 1 | 900 |
| $C_2H_5$ | $C_2H_5$ | H | 1 | 300 |
| morpholino | | H | 1 | 300 |
| N-methylpiperazino | | H | 0.3 | 900 |
| pyrrolidino | | H | 0.03 | 100 |
| piperidino | | H | 0.1 | 300 |

The compound marked with an asterisk [7-(2-hydroxy-3-methylaminopropoxy)-2,2-dimethyl-4-phenylchroman hydrochloride] was found to have an oral LD$_{50}$ of greater than 100 mg/kg in mice.

In a further aspect the present invention provides a process for the preparation of compounds of the formula (I) wherein R$_3$ is a hydrogen atom which comprises the reaction of an amine HNR$_1$R$_2$ and a compound of the formula (IX):

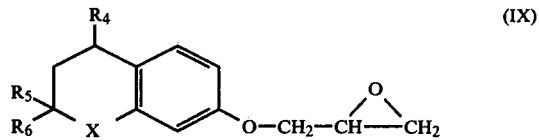

(IX)

wherein X, R$_4$, R$_5$ and R$_6$ are as defined in relation to formula (I).

Such reaction may take place at any non-extreme temperature, for example, −20° C. to 120° C., although roughly ambient or slightly elevated temperatures, for example, 12° C.-80° C. are generally most convenient.

The reaction is normally carried out in an inert organic solvent such as a lower alkanol, for example, ethanol.

The useful intermediates of the formula (IX) form an aspect of this invention.

A closely related method of preparing the compounds of formula (I) wherein R$_3$ is a hydrogen atom comprises the reaction of an amine HNR$_1$R$_2$ with a compound of the formula (X):

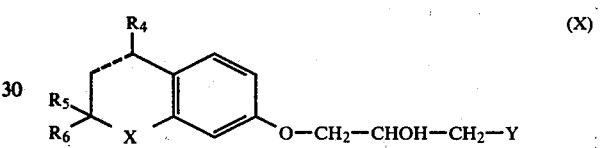

(X)

wherein X, R$_4$, R$_5$ and R$_6$ are as defined in relation to formula (I) and Y is a group displaceable by a nucleophilic centre such as an amine nitrogen atom.

Most suitably Y is Cl, Br, I, OSO$_2$CH$_3$, OSO$_2$C$_6$H$_4$CH$_3$ or other conventional good leaving groups.

The preceding reaction may take place under reaction conditions similar for that of the reaction of an amine with the epoxide (IX).

Compounds of the formula (I) wherein R$_1$ and R$_2$ are both C$_{1-4}$ alkyl groups may be prepared by alkylation of the corresponding primary or secondary amine, for example, by alkylation with formaldehyde/formic acid.

Compounds of the formula (I) wherein R$_1$ is a C$_{1-4}$ alkyl group may be prepared from the corresponding compound wherein R$_1$ is a hydrogen atom by alkylation, for example, by reaction with an alkyl halide or the like.

The epoxides of the formula (IX) may be prepared by the reaction of 1-chloro-2,3-epoxoxypropane and a compound of the formula (XI):

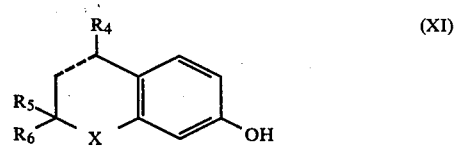

(XI)

wherein X, R$_4$, R$_5$ and R$_6$ are as defined in relation to formula (I), or an alkali metal salt thereof.

The preceding reaction may conveniently be carried out in an inert organic solvent such as acetone at a non-extreme temperature in the presence of a mild base such as potassium carbonate.

A further process for the preparation of the compounds of the formula (I) comprises the reaction of a compound of the formula (XII):

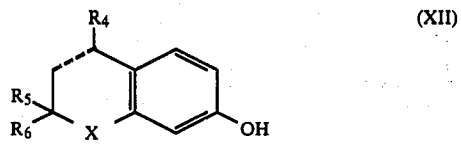

or a salt thereof wherein X, $R_4$, $R_5$ and $R_6$ are as defined in relation to formula (I) with a compound of the formula (XIII):

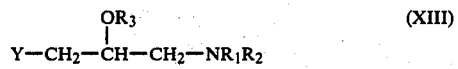

or a salt thereof wherein $R_1$, $R_2$ and $R_3$ are as defined in relation to formula (I) and Y is as defined in relation to formula (X).

Such reactions may take place under conditions similar to those described for the reaction of a compound of the formula (XI) with 1-chloro-2,3-epoxypropane.

The compounds of the formula (I) wherein $R_3$ is a $C_{1-4}$ acyl group and $R^1$ and $R^2$ are not hydrogen atoms, may be prepared from the compounds of the formula (I) wherein $R_3$ is hydrogen by conventional acylation methods well known to those skilled in the art, for example, by the reaction of a compound of the formula (I) wherein $R_3$ is hydrogen with an acyl halide, for example, acetyl chloride, in an inert solvent, for example, tetrahydrofuran, optionally in the presence of a base, for example sodium hydride.

The compounds of the formula (I) wherein $R_3$ is a $C_{1-4}$ alkyl group and $R_2$ is not a hydrogen atom may be prepared by the hydrogenolysis of a compound of the formula (XIV):

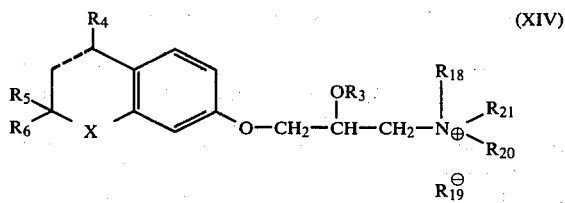

wherein X, $R_4$, $R_5$ and $R_6$ as defined in relation to formula (I), $R_3$ is a $C_{1-4}$ alkyl group, $R_{18}$ is a group removable by hydrogenolysis; $R_{19}$ is a halogen atom; $R_{20}$ is a $C_{1-4}$ alkyl or benzyl group; and $R_{21}$ is a $C_{1-4}$ alkyl group or is joined to $R_{20}$ so that the $NR_{21}R_{20}$ moiety is a 5-, 6- or 7-membered saturated heterocyclic group.

Suitably $R_{18}$ is a benzyl group and $R_{19}$ is a chlorine or bromine atom.

The above hydrogenolysis reaction will normally be carried out in the presence of hydrogen and a transition metal catalyst, for example, palladium on charcoal, in a solvent inert under the reaction conditions, for example, a $C_{1-4}$ alkanol such as ethanol.

Compounds of the formula (XIV) may be prepared from the corresponding compounds of the formula (I) wherein $R_3$ is a hydrogen atom and $R_1$ and $R_2$ are not both hydrogen by the formation of a quaternary ammonium salt followed by the alkylation of this quaternary ammonium salt. Both reactions are performed by conventional techniques well known to those skilled in the art.

The compounds of the formula (I) wherein $R_3$ is a $C_{1-4}$ alkyl group may also be prepared by the alkylation of the corresponding compound of the formula (I) wherein $R_3$ is a hydrogen atom under acid conditions in a conventional manner. However, this is not in general a preferred method of preparing these compounds due to the formation of a number of side-products.

The compounds of the formula (XI) may be prepared by processes such as those outlined in the following reaction schemes.

Scheme 1

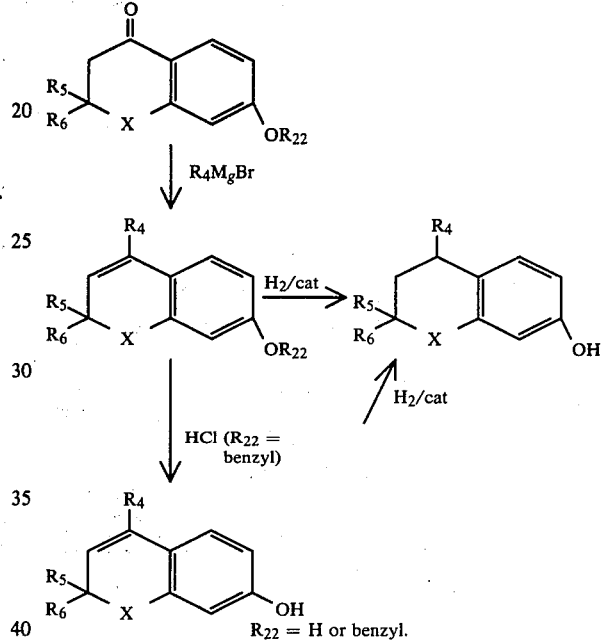

$R_{22}$ = H or benzyl.

Scheme 2

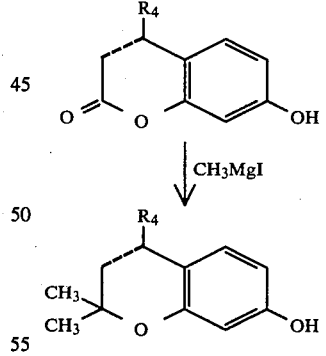

Compounds of the formula (I) wherein the dotted line represents a single bond may be prepared by the reduction of the compound of the formula (I) wherein the dotted line represents a double bond by a reducing agent capable of reducing the vinylic double bond. Suitable reducing agents are described in Belgian Pat. No. 831939.

Belgian Pat. No. 831939 describes the preparation of compounds related to the compounds of this invention and illustrates the preparation of intermediates by the process outlined in the preceding reaction schemes.

The following Examples illustrate the invention.

EXAMPLE 1

7-(2,3-Epoxypropoxy)-2,2-dimethyl-4-phenylchroman

A mixture of 7-hydroxy-2,2-dimethyl-4-phenylchroman (11.8 g, 0.046 mole), anhydrous potassium carbonate (11.7 g, 0.093 mole), epichlorohydrin (50 ml) and dry acetone (50 ml) was stirred and boiled under reflux for 6 hours, then cooled and filtered. The filtrate was evaporated in vacuo and the residual brown oil dissolved in ether, washed with water and dried (magnesium sulphate). Removal of the solvent gave 7-(2,3-epoxypropoxy)-2,2-dimethyl-4-phenylchroman as a pale brown solid (13.56 g, 95%), m.p. 82°–85°, after crystallisation from ethanol.

EXAMPLE 2

7-(2-Hydroxy-3-dimethylaminopropoxy)-2,2-dimethyl-4-phenylchroman

A mixture of 7-(2,3-epoxypropoxy)-2,2-dimethyl-4-phenylchroman (6.1 g), anhydrous dimethylamine (15 ml) and ethanol were left to stand at ambient temperature until tlc showed that reaction was complete (c. 2 hrs.). Removal of the solvent in vacuo gave 7-(2-hydroxy-3-dimethylaminopropoxy)-2,2-dimethyl-4-phenylchroman (6.8 g, 97%) isolated as the hydrochloride salt, m.p. 210°–215°, from acetone-ethanol.

EXAMPLE 3

7-(2-Hydroxy-3-isopropylaminopropoxy)-2,2-dimethyl-4-phenylchroman

A mixture of 7-(2,3-epoxypropoxy)-2,2-dimethyl-4-phenylchroman (6.35 g.), isopropylamine (16 ml) and ethanol (16 ml) was boiled under reflux for 2 days. Removal of the solvent in vacuo gave 7-(2-hydroxy-3-isopropylaminopropoxy)-2,2-dimethyl-4-phenylchroman (6.7 g., 73%) isolated as the hydrochloride salt, m.p. 171°–174° from ether-ethanol.

EXAMPLE 4

7-(2-Hydroxy-3-methylaminopropoxy)-2,2-dimethyl-4-phenylchroman

Reaction of 7-(2,3-epoxypropoxy)-2,2-dimethyl-4-phenylchroman with methylamine by an analogous method to that described in Example 2 gave 7-(2-hydroxy-3-methylaminopropoxy)-2,2-dimethyl-4-phenylchroman isolated as its hydrochloride salt, (57%), m.p. 182°–183°.

EXAMPLES 5-10

The following compounds were prepared by an analogous method to that described in Example 3:

7-[2-Hydroxy-3-(1-piperidino)propoxy]-2,2-dimethyl-4-phenylchroman; hydrochloride salt m.p. 190°–192°.

7-[2-Hydroxy-3-(1-morpholino)propoxy]-2,2-dimethyl-4-phenylchroman; hydrochloride salt m.p. 170°–171°.

7-[2-Hydroxy-3-(1-pyrrolidino)propoxy]-2,2-dimethyl-4-phenylchroman; m.p. 81°–83°.

7-[2-Hydroxy-3-(4-methyl-1-piperazino)propoxy]-2,2-dimethyl-4-phenylchroman; dihydrochloride salt m.p. 238°–240°.

7-[2-Hydroxy-3-diethylaminopropoxy]-2,2-dimethyl-4-phenylchroman; m.p. 69°–71°.

7-[2-Hydroxy-3-tert-butylaminopropoxy]-2,2-dimethyl-4-phenylchroman; hydrochloride salt m.p. 201°–204°.

EXAMPLE 11

4-(3-Trifluoromethylphenyl)-7-(2-hydroxy-3-methylaminopropoxy)2,2-dimethylchroman Reaction of 4-(3-Trifluoromethylphenyl)-2,2-dimethyl-7-chromanol with epichlorohydrin, by an analogous method to that described in Example 1, gave 7-(2,3-epoxypropoxy)-4-(3-trifluoromethylphenyl)-2,2-dimethylchroman. Reaction of this epoxide with methylamine, by an analogous method to that described in Example 2 gave 4-(3-trifluoromethyl-phenyl-7-(2-hydroxy-3-methylaminopropoxy)-2,2-dimethylchroman, (benzoate salt, m.p. 145°–157°).

The corresponding 3-dimethylaminopropoxy compound, isolated as its hydrochloride salt m.p. 211°–214°, was prepared in an analogous manner.

EXAMPLE 12

7-(2-Hydroxy-3-dimethylaminopropoxy)-2,2-dimethyl-4-phenyl-2H-chromene

Reaction of 2,2-dimethyl-4-phenyl-2H-chromen-7-ol with epichlorohydrin, by an analogous process to that described in Example 1 gave 7-(2,3-epoxypropoxy)-2,2-dimethyl-4-phenyl-2H-chromene (78%). Reaction of this epoxide with dimethylamine by an analogous process to that described in Example 2 gave 7-(2-hydroxy-3-dimethylaminopropoxy)-2,2-dimethyl-4-phenyl-2H-chromene isolated as its hydrochloride salt (48%), m.p. 208°–209°.

EXAMPLE 13

7-(2-Hydroxy-3-dimethylaminopropoxy)-2,2-dimethyl-4-(2-naphthyl)chroman 3,4-Dihydro-7-hydroxy-4-(2-naphthyl)coumarin, m.p. 159°–162°, was prepared by the condensation of resorcinol with 3-(2-naphthyl)acrylic acid in the presence of concentrated hydrochloric acid (method of Simpson and Stephen, J. Chem. Soc. 1956, 1382).

Reaction of the dihydrocoumarin with methyllithium gave crude 4-(2,4-dihydroxyphenyl)-2-methyl-4-(2-naphthyl)-2-butanol which was cyclised with p-toluenesulphonic acid in benzene to give 2,2-dimethyl-4-(2-naphthyl)-7-chromanol m.p. 189°–191°. Reaction of this chromanol with epichlorohydrin, by an analogous process to that described in Example 1, gave 7-(2,3-epoxypropoxy)-2,2-dimethyl-4-(2-naphthyl)chroman which on reaction with dimethylamine by an analogous process to that described in Example 2, gave 7-(2-hydroxy-3-dimethylamino-propoxy)-2,2-dimethyl-4-(2-napthyl)-chroman isolated as the hydrochloride salt (48%), m.p. 240°–247°.

EXAMPLE 14

7-(2-Hydroxy-3-methylaminopropoxy)-2,2-dimethyl-4-(2-naphthyl)chroman

Reaction of 7-(2,3-epoxypropoxy)-2,2-dimethyl-4-(2-naphthyl)chroman with methylamine, by an analogous method to that described in Example 2 gave 7-(2-hydroxy-3-methylaminopropoxy)-2,2-dimethyl-4-(2-naphthyl)chroman isolated as its hydrochloride salt m.p. 183°–188°.

EXAMPLE 15

3,4-Dihydro-7-hydroxy-4-(1-naphthyl)coumarin

A mixture of 3-(1-naphthyl)acrylic acid (50.0 g., 0.25 moles) in concentrated hydrochloric acid (1500 ml.)

was stirred at reflux while a vigorous stream of hydrogen chloride was passed through the reaction for 6 hours. The solution was allowed to stand overnight at room temperature, then filtered to give a white solid which was dissolved in ethyl acetate and washed with saturated sodium bicarbonate solution (3×). The ethyl acetate solution was dried and removal of solvent gave the dihydrocoumarin as a white solid (43.5 g., 85% based on consumed starting material) m.p. 193°–196° C.

EXAMPLE 16

2,2-Dimethyl-4-(1-naphthyl)-7-chromanol

To a stirred solution of methyl-lithium in ether (120 ml., 1.9 M solution) at room temperature was added over 0.5 hours finely powdered 3,4-dihydro-7-hydroxy-4-(1-napthyl) coumarin (14.5 g, 0.05 moles). After refluxing for 1 hour a purple solid precipitated out of solution and the reaction mixture was allowed to cool, acidified with dilute hydrochloric acid and extracted with ether (3×). The combined ether extracts were dried and removal of solvent gave a dark coloured oil which was refluxed overnight in glacial acetic acid. The glacial acetic acid was removed in vacuo and the residue dissolved in ether, washed with water, saturated sodium bicarbonate solution and dried. Removal of solvent gave an extremely viscous oil, column chromatography of which on silica, eluting with 40°–60° petrol: ether (gradually increasing concentration of ether) gave the required chroman as a low melting pale yellow solid (9.4 g., 76%).

EXAMPLE 17

7-(2,3-Epoxypropoxy(-2,2-dimethyl-4-(1-naphthyl)-chroman 2,2-Dimethyl-4-(1-naphthyl)-7-chromanol (6.98 g., 0.02 moles) and epichlorohydrin (22 ml.) were dissolved in acetone (22 ml.). Potassium carbonate (4.7 g.) was added and the mixture refluxed for 6 hours, allowed to cool and filtered. The acetone was removed in vacuo and the residue dissolved in ether, washed with water and dried. Removal of solvent gave the title epoxide as a dark coloured oil (6.28 g, 81%) which was used in the next reaction without purification.

EXAMPLE 18

4-(1-Naphthyl)-2,2-dimethyl-7-(3-dimethylamino-2-hydroxypropoxy)chroman 7-(2,3-Epoxypropoxy)-2,2-dimethyl-4-(1-naphthyl)-chroman (3.15 g., 0.0088 moles) was dissolved in a solution of dimethylamine in ethanol (20 ml., ~40%) and left to stand at room temperature for 48 hours. Removal of solvent gave the title compound as a dark coloured oil which was converted to the succinate salt. Recrystallization from acetone gave a white solid (1.72 g., 49%) m.p. 123°–125° C.

EXAMPLE 19

4-(1-Naphthyl)-2,2-dimethyl-7-(3-methylamino-2-hydroxypropoxy)chroman

Methylamine (7 ml) was added to 7-(2,3-epoxypropoxy)-2,2-dimethyl-4-(1-naphthyl)chroman (3.3 g., 0.0092 moles) in ethanol (7 ml) and the solution left to stand at room temperature for 48 hours. Removal of solvent gave the title compound as a dark coloured oil which was converted to the hydrochloride salt. Recrystallization from 1:1 petroleum ether:ether gave a grey solid (0.85 g., 24%) m.p. 96°–100° C.

EXAMPLE 20

7-Hydroxy-4-(1-naphthyl)coumarin

A solution of resorcinol (4.84 g., 0.041 moles) and ethyl 1-naphthoylacetate (10 g., 0.041 moles) in ethanol (50 ml.) was saturated with hydrogen chloride at room temperature (cooling with ice/water) and left to stand in s stoppered flask for 24 hours. The solution was filtered to give the required coumarin as an orange solid (7.8 g., 66%, m.p. 292°–295° C.

EXAMPLE 21

2,2-Dimethyl-4-(1-naphthyl)-2H-chromen-7-ol

To a stirred solution of methyl-lithium in ether (60 ml, 2 M solution) at room temperature was added over 0.5 hours 7-hydroxy-4-(1-naphthyl)coumarin (7.5 g, 0.025 moles). The reaction mixture was refluxed for 2 hours, allowed to cool and decomposed by the addition of dilute hydrochloric acid. The organic layer was separated, the aqueous layer extracted with ether (2x) and the combined organic extracts washed with water and dried. Removal of solvent gave the required title chromene as an orange oil (7.22 g, 95%).

EXAMPLE 22

7-(2,3-Epoxypropoxy)-2,2-dimethyl-4-(1-naphthyl)-2H-chromene 2,2-Dimethyl-4-(1-naphthyl)-2H-chromen-7-ol (7.92 g, 0.026 moles) and epichlorohydrin (28,5 ml) were dissolved in acetone (50 ml). Potassium carbonate (6.3 g), was added and the mixture refluxed for 6 hours, allowed to cool and filtered. The acetone was removed in vacuo and the residue dissolved in ether, washed with water and dried. Removal of solvent gave the title product as an orange oil (8.1 g, 86%) which was used in the next reaction without further purification.

EXAMPLE 23

4-(1-Naphthyl)-2,2-dimethyl-7-(3-dimethylamino-2-hydroxpropoxy)-2H chromene 7-(2,3-Epoxypropoxy)-2,2-dimethyl-4-(1-naphthyl)-2H-chromene (4.4 g., 0.012 moles) was dissolved in a solution of dimethylamine in ethanol (28 ml., ~40% solution) and left to stand at room temperature for 48 hours. Removal of solvent gave the title product as an orange oil which was converted to the hydrochloride salt. Recrystallization from acetone gave a white solid (3.13 g., 64%) m.p. 185°–187° C.

EXAMPLE 24

4-(1-Naphthyl)-2,2-dimethyl-7-(3-methylamino-2-hydroxypropoxy)-2H chromene

Methylamine (9.5 ml) was added to 7-(2,3-epoxypropoxy)-2,2-dimethyl-4-(1-naphthyl)-2H chromene (4.5 g., 0.013 moles) in ethanol (9.5 ml) and the solution left to stand at room temperature for 48 hours. Removal of solvent gave the title compound as an orange oil (3.2 g., 63%). N.M.R. ($\tau$CDCl$_3$) 8.54(s, 3H, CH$_3$—), 8.48(s, 3H, CH$_3$—), 7.06(s, 3H, N—CH$_3$), 6.72(d, 2H, —CHC-H$_2$—), 6.05(d, 2H, —CH$_2$CH—), 4.31(s. 1H, vinylic CH), 3.40–3.80 (m, 3H, aromatic H's), 2.10–2.75 (m, 7H, aromatic H's).

EXAMPLE 25

4-(4-Trifluoromethylphenyl)-7-(2-hydroxy-3-dimethylaminopropoxy)-2,2-dimethylchroman The above compound, isolated as its hydrochloride salt m.p. 204°–207°, was prepared in an analogous manner to the corresponding 3-trifluoromethyl compound.

EXAMPLE 26

7-(2-Acetoxy-3-dimethylaminopropoxy)-2,2-dimethyl-4-(3-trifluoromethylphenyl)chroman hydrobromide Sodium hydride (0.4 g) was added to a solution of 2,2-dimethyl-7-(3-dimethylamino-2-hydroxy-propyloxy)-4-(3-trifluoromethylphenyl)chroman (4 g) in dry tetrahydrofuran. Acetyl chloride (0.8 ml) was added giving an instantaneous white precipitate. Water was added and the mixture extracted with ether. Removal of the solvent under reduced pressure gave an oil which was chromatographed on alumina. Elution with ether-petrol (1:1) gave a colourless oil (1.5 g). Treatment of this with ethereal hydrogen bromide gave the title compound as an off-white foam. Found C 53.57, H 6.23, N 2.49; $C_{25}H_{31}NO_4F_3Br \cdot 1H_2O$ requires C 53.19, H 5.89, N 2.48%. $\tau$ ($CDCl_3$) freebase 8.65 (3H,s), 8.55 (3H,s) 8.15–7.95 (2H,m), 7.95 (3H,s), 7.75 (6H,s), 7.45 (2H,d), 5.95 (2H,d), 5.65–5.9 (1H,m), 4.75 (1H,dt), 3.75–3.35 (3H,m), 2.75–2.3 (4H,m). $\tau$ ($CDCl_3$) HBr salt. 8.7 (3H,s), 8.6 (3H,s), 8.15–7.95 (2H,m), 7.8 (3H,s), 7.13 (3H,d) and 7.03 (3H,d) (both collapse to a common singlet with $D_2O$) 6.45 (2H,t, collapses to a doublet with $D_2O$), 5.85 (3H,m), 4.3 4.3 (1H, dt), 3.8–3.3 (3H, m), 2.8–215 (4H, m), ~4–3 (1H diffuse, disappears with $D_2O$).

EXAMPLE 27

2,2-dimethyl-7-(3-dimethylamino-2-methoxypropoxy)-4-(3-trifluoromethylphenyl)chroman 2,2-dimethyl-7-(3-dimethylamino-2-hydroxypropoxy)-4-(3-trifluoromethylphenyl)chroman (5 g) in benzene was added to benzyl bromide (10 ml) in benzene and the solution left to stand 15 hrs. Removal of the solvent under reduced pressure and trituration of the oil with petrol gave the quaternary salt.

To this salt (1.5 g) in dichloromethane (20 ml) was added 50% aqueous sodium hydroxide (5 ml) followed by dimethyl sulphate (1.2 ml). This was left to stir for 2 hrs. and concentrated ammonia solution (1 ml) added. The mixture was acidified (2 N.HCl), extracted with chloroform and the organic layer dried. Removal of the solvent under reduced pressure gave an oil which was dissolved in ethanol and hydrogenated using 10% Pd/c as catalyst. Filtration of the mixture through celite and removal of the solvent under reduced pressure gave an oil which when basified (2 N NaOH) and extracted with ether had spectroscopic properties were consistent with the title compound. $\gamma$($CDCl_3$), 8.67 (3H,s), 8.59 (3H,s) 8.15–7.95 (2H,m), 7.7 (6H,s), 7.5 (2H,d, J=6H_2), 6.51 (3H,s), 6.4–5.7 (4H,m), 3.7–3.3 (3H,m), 2.9–2.3 (4H,m).

What we claim is:

1. A compound of the formula (I):

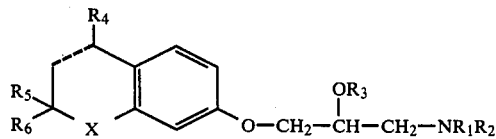

(I)

or a pharmaceutically acceptable salt thereof wherein the $NR_1R_2$ moiety is a 5-, 6-, or 7-membered saturated heterocyclic ring; $R_3$ is hydrogen, alkyl of 1 to 4 carbon atoms or acyl of 1 to 4 carbon atoms; $R_4$ is naphthyl or phenyl unsubstituted or substituted by one or two substituents selected from the group consisting of fluorine, chlorine, bromine, methoxyl, benzyloxyl, trifluoromethyl, methyl, cyano, nitro, acetoxyl, amino, methylamino, ethylamino, dimethylamino, diethylamino, acetamido, hydroxyl, methoxycarbonyl, ethoxycarbonyl, carboxamido, sulphonamido, carboxy, trifluoromethylthio, trifluoromethoxyl, methylsulphonyl, trifluoromethylsulphonyl and methylthio; $R_5$ is hydrogen or alkyl of 1 to 4 carbon atoms; $R_6$ is hydrogen or alkyl of 1 to 4 carbon atoms; X is oxygen and the dotted line represents a single or double bond.

2. A compound according to claim 1 wherein the $NR_1R_2$ moiety forms a piperidino, morpholino, pyrrolidino or piperazino ring.

3. A compound according to claim 1 wherein the dotted line represents a single bond.

4. A compound according to claim 1 wherein $R_3$ is hydrogen, $R_4$ is naphthyl and $R_5$ and $R_6$ are each methyl.

5. A compound according to claim 1 wherein $R_3$ is hydrogen.

6. A compound according to claim 1 wherein $R_4$ is phenyl, naphthyl or phenyl substituted by fluorine, chlorine, bromine, methoxyl, benzyloxyl, trifluoromethyl, methyl or nitro.

7. A compound according to claim 1 wherein $R_5$ and $R_6$ are each methyl.

8. A compound according to claim 1 of the formula (II):

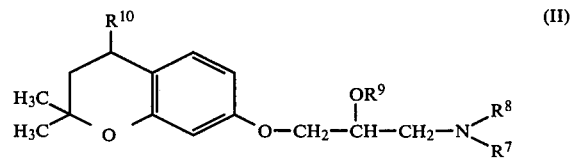

(II)

or a pharmaceutically acceptable salt thereof, wherein $R^8$ is linked to $R^7$ so that the moiety $NR^7R^8$ forms a 5- or 6- membered saturated heterocyclic ring; $R^9$ is hydrogen or acetyl; and $R^{10}$ is phenyl, naphthyl, or phenyl substituted by fluorine, chlorine, bromine, methoxyl, benzyloxyl, trifluoromethyl, methyl, cyano, nitro, acetoxyl, amino, methylamino, ethylamino, dimethylamino, diethylamino, acetamido, hydroxyl, methoxycarbonyl, ethoxycarbonyl, carboxamido, sulphonamido, carboxy, trifluoromethylthio, trifluoromethoxyl, methylsulphonyl, trifluoromethylsulphonyl or methylthio.

9. A compound according to claim 8 wherein $R^8$ is linked to $R^7$ so that the moiety $NR^7R^8$ forms a piperidino, morpholino, pyrrolidino or piperazino ring.

10. A compound according to claim 8 wherein $R^9$ is hydrogen.

11. A compound according to claim 8 wherein $R^{10}$ is phenyl, 2-naphthyl, or phenyl substituted by fluorine, chlorine, bromine, methyl, methoxy, hydroxy, trifluoromethyl or nitro.

12. A compound according to claim 1 of the formula (III):

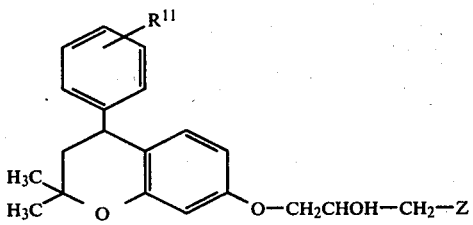

or a pharmaceutically acceptable salt thereof, wherein $R^{11}$ is hydrogen, fluorine, chlorine, bromine, methyl, methoxy, or trifluoromethyl and Z is morpholino, piperidino, pyrrolidino or N-methylpiperazino.

13. A compound according to claim 12 wherein $R^{11}$ is hydrogen, fluorine, chlorine, methyl, methoxy or trifluoromethyl.

14. A compound according to claim 12 wherein $R^{11}$ is trifluoromethyl.

15. A compound according to claim 14 wherein $R^{11}$ is 3-trifluoromethyl.

16. A compound according to claim 12 wherein $R^{11}$ is hydrogen.

17. A compound according to claim 1 of the formula (IV) or (V):

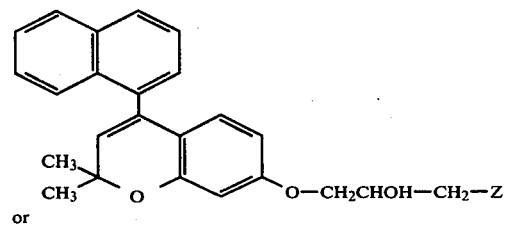

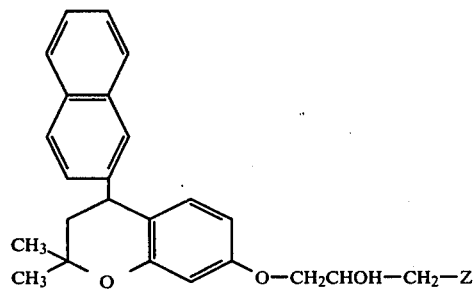

wherein Z is morpholino, piperidino, pyrrolidino or N-methylpiperazino.

18. The compound according to claim 1 which is 7-[2-hydroxy-3-(1-piperidino)propoxy]-2,2-dimethyl-4-phenylchroman or a pharmaceutically acceptable acid addition salt thereof.

19. The compound according to claim 1 which is 7-[2-hydroxy-3-(1-morpholino)propoxy]-2,2-dimethyl-4-phenylchroman or a pharmaceutically acceptable acid addition salt thereof.

20. The compound according to claim 1 which is 7-[2-hydroxy-3(1-pyrrolidino)propoxy]-2,2-dimethyl-4-phenylchroman or a pharmaceutically acceptable acid addition salt thereof.

21. The compound according to claim 1 which is 7-[2-hydroxy-3-(4-methyl-1-piperazino)propoxy]-2,2-dimethyl-4-phenylchroman or a pharmaceutically acceptable acid addition salt thereof.

22. A compound according to claim 14 in the form of a pharmaceutically acceptable acid addition salt.

23. A compound selected from the group consisting of a chroman derivative of the formula:

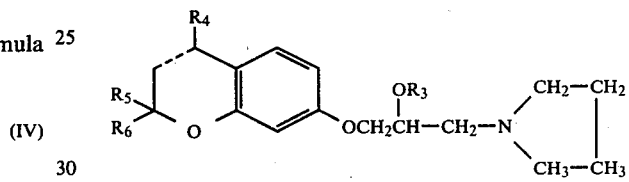

and the pharmaceutically acceptable salts thereof wherein $R_3$ is hydrogen, alkyl of 1 to 4 carbon atoms or acyl of 1 to 4 carbon atoms;

$R_4$ is naphthyl or phenyl unsubstituted or substituted with one or two members selected from the group consisting of fluoro, chloro, bromo, methoxy, benzyloxy, trifluoromethyl, methyl, cyano, nitro, acetoxy, amino, methylamino, ethylamino, dimethylamino, diethylamino, acetamido, hydroxy, carbomethoxy, carbethoxy, carboxamido, sulphonamido, carboxy, trifluoromethylthio, trifluoromethoxy, methylsulphonyl, trifluoromethylsulphonyl and methylthio;

each of $R_5$ and $R_6$ is hydrogen or alkyl of 1 to 4 carbon atoms; and the dotted line is a single or double bond.

* * * * *